(12) United States Patent
Faragalla

(10) Patent No.: US 7,485,101 B1
(45) Date of Patent: *Feb. 3, 2009

(54) MULTIPLE SHOCKWAVE FOCAL TREATMENT APPARATUS WITH TARGETING POSITIONING AND LOCATING APPARATUS

(76) Inventor: Yousry B. Faragalla, FMD, LLC, P.O. Box 1500, Lorton, VA (US) 22199

(*) Notice: Subject to any disclaimer, the term of this patent is extended or adjusted under 35 U.S.C. 154(b) by 654 days.

This patent is subject to a terminal disclaimer.

(21) Appl. No.: 10/891,427

(22) Filed: Jul. 15, 2004

Related U.S. Application Data

(63) Continuation-in-part of application No. 10/102,640, filed on Mar. 22, 2002, now Pat. No. 6,780,161.

(51) Int. Cl.
*A61B 1/00* (2006.01)
(52) U.S. Cl. ............... 601/2; 601/1; 601/3; 600/437; 600/439
(58) Field of Classification Search ............ 601/1–3; 600/437–459, 410, 411, 429
See application file for complete search history.

(56) References Cited

U.S. PATENT DOCUMENTS

| 3,942,531 | A | | 3/1976 | Hoff et al. | |
|---|---|---|---|---|---|
| 4,896,673 | A | * | 1/1990 | Rose et al. ............... | 600/439 |
| 5,209,221 | A | | 5/1993 | Riedlinger et al. | |
| 5,219,401 | A | | 6/1993 | Cathignol et al. | |
| 5,301,659 | A | * | 4/1994 | Brisson et al. ............... | 601/4 |
| 5,350,351 | A | * | 9/1994 | Saffer ............... | 601/2 |
| 5,395,299 | A | * | 3/1995 | Herrmann et al. ............... | 601/2 |
| 5,399,146 | A | * | 3/1995 | Nowacki et al. ............... | 601/4 |
| 5,409,002 | A | * | 4/1995 | Pell ............... | 600/407 |
| 5,435,304 | A | * | 7/1995 | Oppelt et al. ............... | 600/439 |
| 5,435,311 | A | * | 7/1995 | Umemura et al. ............... | 600/439 |
| 5,468,214 | A | * | 11/1995 | Herrmann et al. ............... | 601/2 |
| 5,582,578 | A | | 12/1996 | Zhong et al. | |
| 6,123,679 | A | | 9/2000 | Lafaut et al. | |
| 6,390,995 | B1 | * | 5/2002 | Ogden et al. ............... | 601/2 |
| 6,546,279 | B1 | * | 4/2003 | Bova et al. ............... | 600/429 |
| 6,780,161 | B2 | * | 8/2004 | Faragalla et al. ............... | 601/2 |

OTHER PUBLICATIONS

Lokhandwalla M et al., Fracture Mechanics Model of Stone Comminution in ESWL and Implications for Tissue Damage, Phys. Med. Biol., 2000; 45; 1-18.

Sher K Z et al., Synchronous Twin Pulse Technique to Improve Efficacy of SWL: Preliminary Results of an Experimental Study, J. of Endourology, 2001; 15; 965-974.

Chuong C.J. et al, Acoustic and Mechanical Properties of Renal Calculi. Implication in SWL, J. of Endourology, 1993; 7: 437.

Church CL, A Theoretical Study of Cavitation Generated by Extra Corporeal Shock Wave Lithotripter, J. Acoustic Soc. Am., 1989; 86: 215.

* cited by examiner

*Primary Examiner*—Long V Le
*Assistant Examiner*—Sanjay Cattungal

(57) ABSTRACT

The present invention relates to a torso-positioning and target-locating apparatus using medical imaging apparatus for treating a living body or tissue with shockwaves originating from at least two sources to a focal area within the living body or tissue.

6 Claims, 4 Drawing Sheets

MULTIPLE SHOCKWAVE FOCAL TREATMENT APPARATUS WITH TARGETING POSITIONING AND LOCATING APPARATUS

REFERENCE TO RELATED APPLICATION

The present application is a continuation-in-part application of application Ser. No. 10/102,640 filed Mar. 22, 2002, now U.S. Pat. No. 6,780,161 entitled APPARATUS FOR EXTRACORPOREAL SHOCKWAVE LITHOTRIPTER USING AT LEAST TWO SHOCKWAVE PULSES, the priority of which is claimed.

FIELD OF INVENTION

The invention relates to a torso positioning and imaging apparatus for improving the efficiency of shockwave treatment in a living body or tissue while, at the same time, reducing the harmful effects of such treatment and to a method of treating a living body or tissue with such an apparatus.

BACKGROUND OF THE INVENTION

In the past two decades, fragmentation of concretions inside a living body by focused shockwaves from outside the body was established as a method of treatment. Recent research is also developing for the application of shockwave treatment in the field of orthopedics and in pathological tissue ablation as well as in other different types of treatment.

The mechanisms by which focused shockwaves disintegrate stones in Extracorporeal Shock Wave Lithotripsy are still not well understood. However, several mechanisms for stone fragmentation have been proposed and documented in the literature.

The shockwave pulse is comprised of a positive peak pressure up to about 120 MPa, which lasts for up to about 2 microseconds followed by negative peak pressure up to about 20 MPa with about 2 to 8 microseconds duration.

It is further known in the art that the negative pressure induces transient cavitation bubbles around the focal point. Ensuing pulses cause these cavitation bubbles to collapse. When bubbles collapse adjacent to a solid surface like a stone, it will take place asymmetrically leading to the formation of high speed, liquid micro jets that hit the stone surface and cause cracking and fragmentation. Only a percentage of these micro jets is directed to the stone while the remaining part is consumed by the adjacent tissues leading to tissue damage.

It is also mentioned in the literature that the conditions required for fracturing stones include one or more of the following: compression and release, tension or spall and cavitation induced stress. Fragmentation involves separation of crystal layers and fracture and cleavage of crystals. The disintegration of stones occurs by the progressive initiation of cracks and their stepwise extension through the material. Brittle materials fail under compressive shock loading by initiation and growth of micro cracks from internal defects such as pores or inclusion or from material boundaries such as interfaces with organic or fibrous material or grain boundaries.

With repeated pulses the micro cracks grow on a prospective spall plane and they coalesce on reaching a critical length creating a fragment. Under pressure, the micro cracks grow in the axial plane; i.e. the failure is in the direction of maximum applied compression that is the direction of shockwave propagation. On the other hand, under tension, micro cracks grow on a plane perpendicular to the direction of applied tension; i.e. perpendicular to the direction of the shockwave propagation.

SUMMARY OF THE INVENTION

In our above-identified application, we disclose that the collapse of the cavitation bubbles can be controlled by the sequential timing and direction of additional shockwaves. Hence, the use of one or more other shockwave sources to generate another shockwave propagating at an appropriate angle from the direction of propagation of the primary shockwave will enhance the treatment effect of shockwaves and abolish or minimize the tissue damage outside the focal area. The value of the angle between these shockwave sources varies according to various factors such as the type of treatment and the level of energy. The timing of generation of shockwaves from these sources could be instantaneous or with a delay period between each of about 1 millisecond up to about 100 milliseconds. This delay varies according to various factors such as the type of treatment and level of energy. The present invention provides a unique support table and medical imaging apparatus, e.g. MRI, x-ray, ultrasound, etc., to facilitate and enhance targeting.

BRIEF DESCRIPTION OF THE DRAWINGS

The above and other objects, advantages and features of the invention will become more apparent when considered with the following specification and accompanying drawings wherein.

DETAILED DESCRIPTION OF THE PREFERRED EMBODIMENT

A preferred embodiment of the present invention comprises the usage of a unique support table 20, x-ray imaging apparatus 30 and ultrasound imaging apparatus 31, 32 and two shockwave sources 10 and 11 where said shockwaves are reaching a focal point or area F2 (which has been located by the medical imaging apparatus, discussed later herein), each from a different angle and the site where treatment is intended is mobilized to be in the focal area F2. Each shockwave source includes a shockwave generator operatively coupled to a reflector. The angle between the two shockwaves is variable, for example from about 67 degrees up to about 105 degrees according to the type of treatment and energy level. However, in a most preferred embodiment, this angle is set at about 90 degrees, i.e. the direction of the propagation of the two shockwaves are almost perpendicular to each other.

Controller CONT (FIG. 4) is provided with a pair of control panels CP-1 and CP-2 which control the power and voltage levels for the shockwave generators 1 and 2 and control the firing rate and delay control for the two shockwave generators to provide the sequential timing discussed earlier herein.

The timing of the generation of the two shockwaves is variable from instantaneous generation to a delay period between the two shockwaves up from about 1 millisecond to about 100 milliseconds. Yet, in the most preferred embodiment, this delay time is set at about 23 milliseconds. Also, according to other embodiments of the invention more than two sources of shockwaves may be involved regardless of the selected angles of directions of generated shockwaves and/or timing of their generation.

It is obvious to those skilled in the art that many modifications and/or alterations may be made within the description of this invention. Any prior art shockwave generator and reflector may be used in the present invention. In a preferred embodiment, Twinheads™, which was using two shockwave generators, has provided good results on experimental testing on in vitro stones. With an angle between axes of the two reflectors about 90 degrees and delay time of firing between the two sources about 23 milliseconds, the shockwave effects became more concentrated in the focal area with disappearance of any effects outside this focal area.

It was found that stone disintegration was limited to the focal area without propagation outside the area F2. Thus, with Twinheads™, damage to the surrounding tissues will be avoided or reduced because of the localization of shockwave effects in the localized focal area. Moreover, the quality of disintegration of stone was finer and more rapid, as it was the result of applying pressure and tension from two different directions to the stone, which enhanced the initiation of cracks and their extension throughout the stone.

Figure 1:
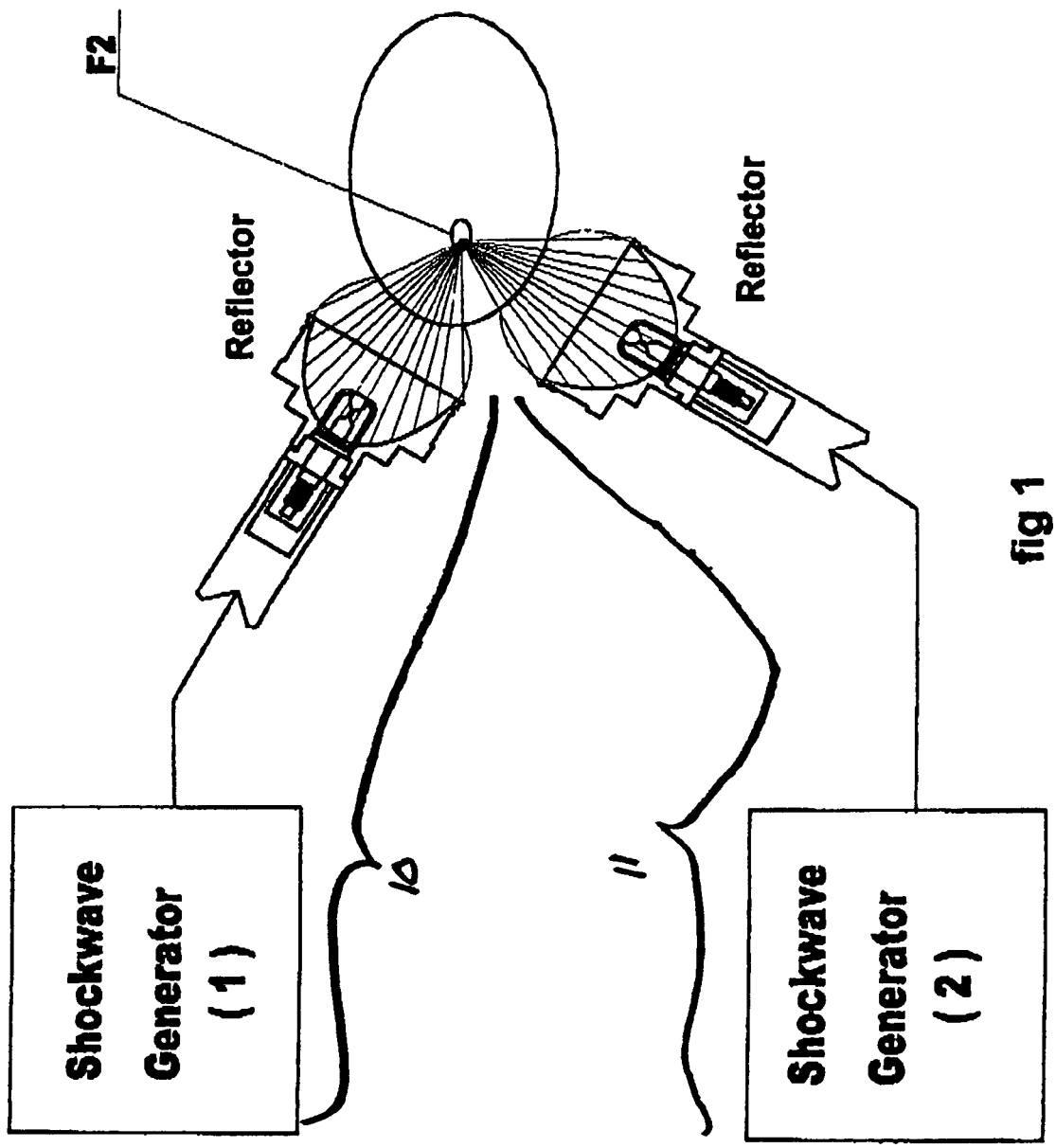
FIG. 1 is a schematic drawing that shows two shockwave generators connected to two reflectors, which are focusing the two shock waves to a focal point F2 inside the living body.
Figure 2:
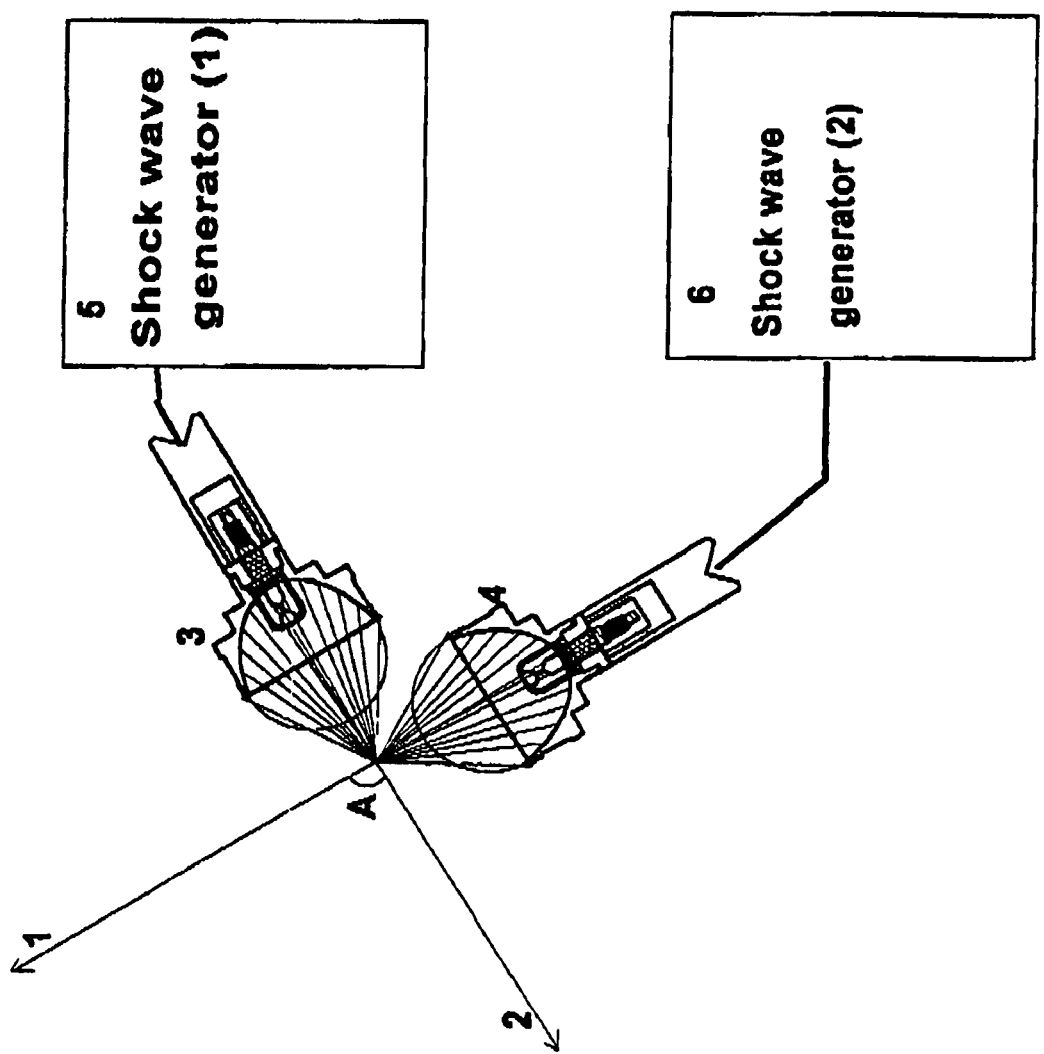
FIG. 2 shows the same configuration where A is the angle between 1 the direction of propagation of shock waves originating from reflector 3 and 2 the direction of propagation of shock waves originating from reflector 4 and where 5 is the first shock wave generator and 6 is the second shock wave generator.
Figure 3:
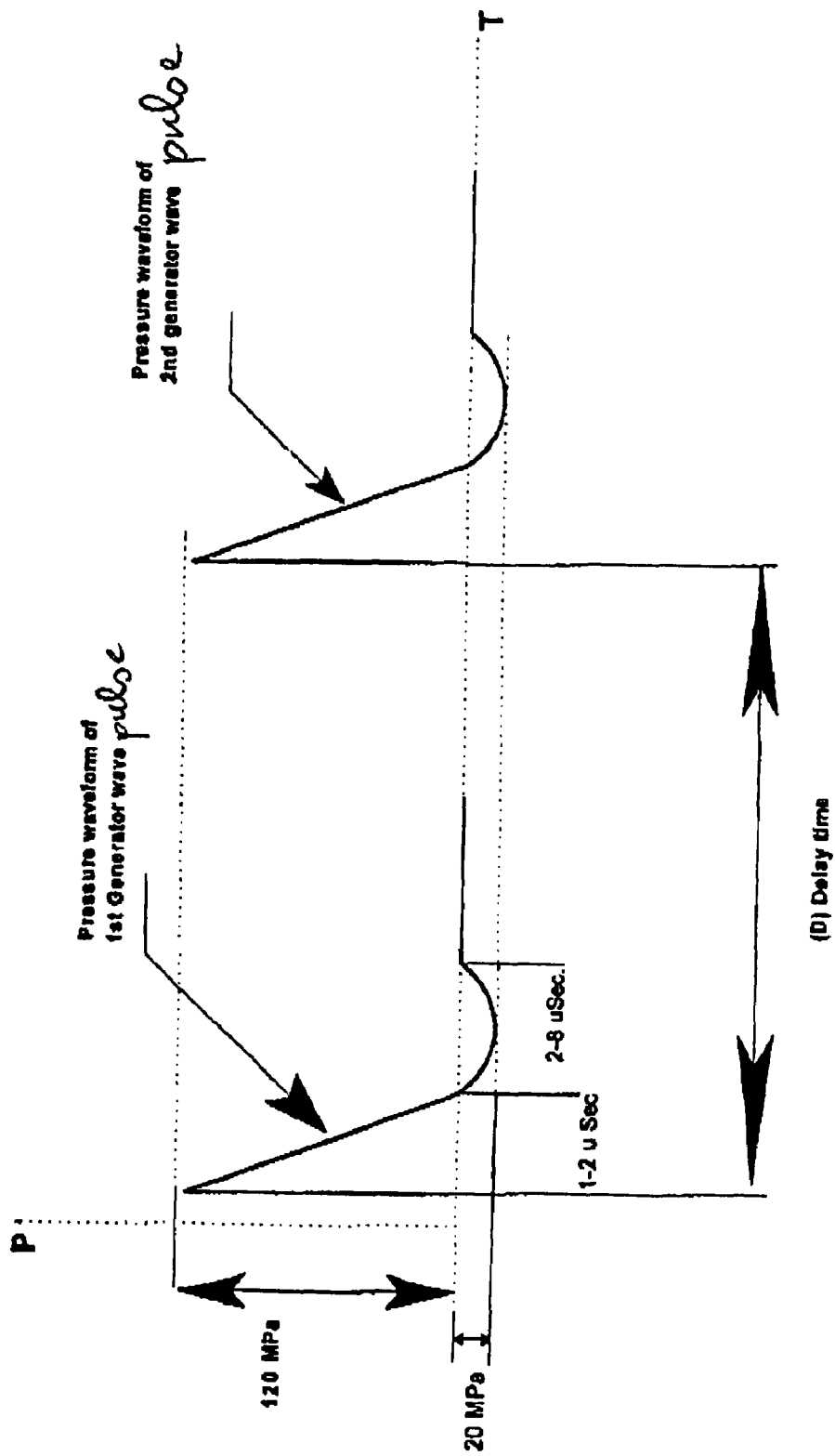
FIG. 3 shows the two shock pulses waveform; one from each of the two shock wave sources and where (D) is the delay time between the two shock waves.
Figure 4:
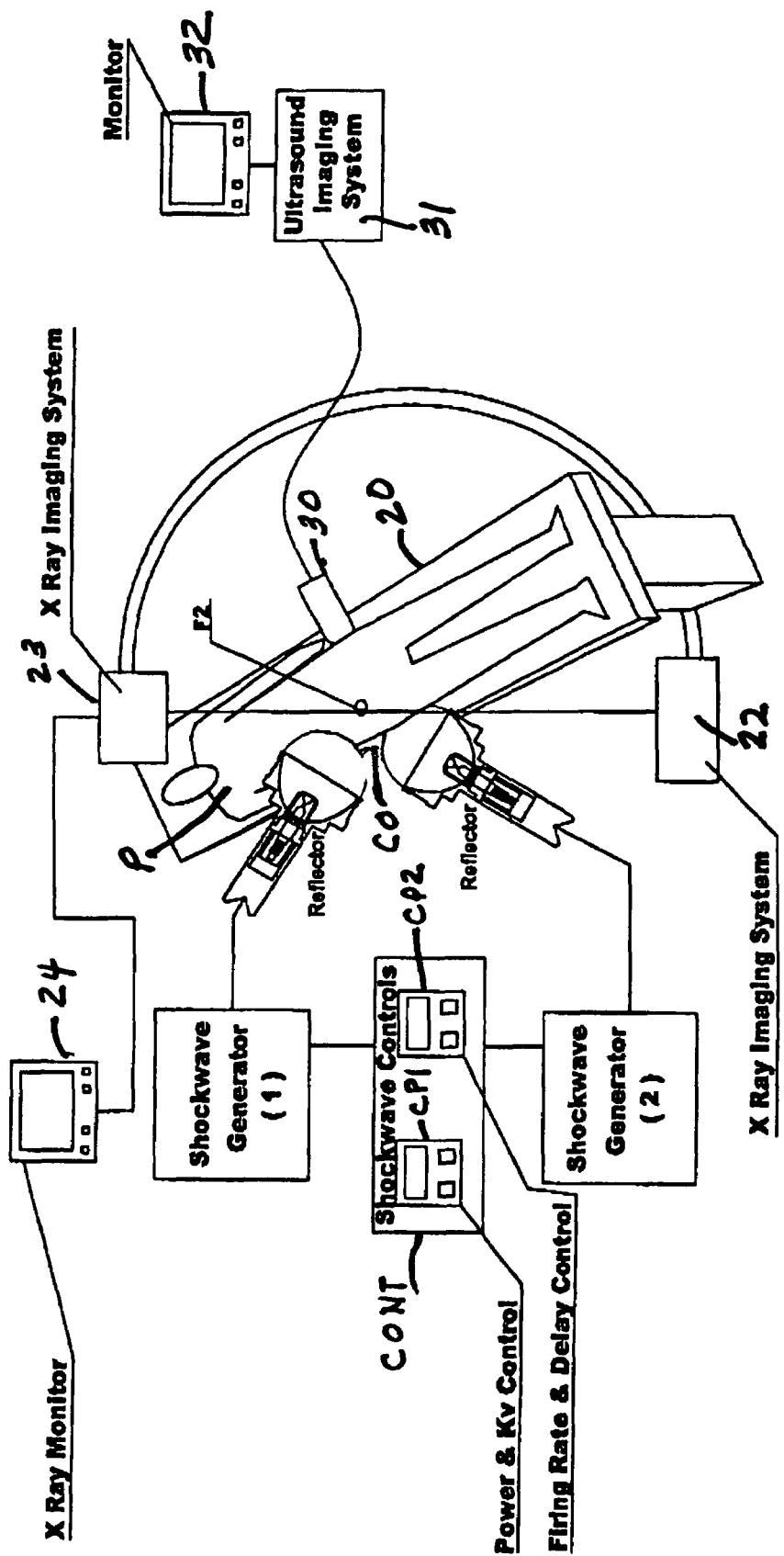
FIG. 4 is a schematic illustration of the invention.

Referring now to FIG. 4 wherein like numerals corresponding to the numerals and letters used in FIGS. 1-3 are repeated therein, a patient P is shown reclining or lying prone face-up on a table 20 having one or more cutout CO with the patient's torso positioned over the cutout CO proximate the location of the stones or area of treatment in the patient. It will be appreciated that the patient P may be lying face down or face up or in other orientations. An x-ray imaging system having an x-ray source 22 and an x-ray detector 23, constituting an x-ray fluoroscopic imaging system and x-ray monitor 24, is used to precisely locate stones or area of treatment in the living body. An ultrasound probe 30 is coupled to an ultrasound imaging system 31 having a monitor 32. In the present case, the patient's body in the area of the kidney stone is coated with an ultrasound gel which couples the ultrasonic energy to the body to do the search or body scan much in the fashion of ultrasound used in maternity situations. The ultrasound imaging system is used to locate the kidney stone or area of treatment and provide an image thereof on the monitor for the operator. These imaging systems are useful to provide an accurate location of where the imaging system is used to provide precise location and imaging of the stones or areas of treatment in the human body. Such imaging systems are also useful to provide images of the results of the shockwave treatments and whether further shockwaves are required. It will be appreciated that the two imaging systems, as well as other imaging systems (CT, MRI, PET), may be used jointly or separately; but preferably both are used on the patient in the same procedure. For safety consideration, since the ultrasound imaging system requires manual movement by an operator of the probe 30 over the human body in the area of the kidney stone or area of treatment, it is done separately from the x-ray imaging procedure. Normal precautions are taken to protect other portions of the patient's body from x-ray radiation.

While the invention has been described in relation to preferred embodiments of the invention, it will be appreciated that other embodiments, adaptations and modifications of the invention will be apparent to those skilled in the art.

What is claimed is:

1. In a shockwave method for fragmenting stones or ablating pathological tissue in a living body wherein at least two shockwave generators are arranged in cooperative relation to each other such that timed sequential shockwave pulses from each said shockwave generators are focused to a focal point at said stones or pathological tissue inside the living body, the improvement comprising using at least two medical imaging systems to precisely locate said stones or pathological tissue and aim said shockwave generators in said living body and controlling the collapse of cavitation bubbles produced by said shockwave pulses by controlling the timing and direction of propagation of each timed shockwave pulse so as to avoid damage to adjacent tissue wherein the directions of propagation between said shockwave pulses has an angle between from about 67° to 105° and wherein said shockwave pulses are generated with a delay time between the two shockwave pulses in the range of 1 millisecond to about 100 milliseconds.

2. The shockwave method defined in claim 1 including providing a body table having a cutout proximate the location of said stones or pathological tissue in said living body, positioning said living body on said body table in a prone position with said stones or pathological tissue in the neighborhood of said cutout using said at least two medical imaging systems through said cutout and contacting said body with said shockwave generators with one of said shockwave generators contacting said living body through said cutout.

3. A shockwave method for fragmenting stones or ablating pathological tissue in a living body or tissue wherein the living body is positioned on a body table having a cutout, and at least two shockwave generators are arranged in cooperative relation to each other and said cutout such that timed sequential shockwave pulses from each said shockwave generators are focused to a focal point at said stones or pathological tissue, and one of said shockwave generators is contacting said living body through said cutout, using x-ray and ultrasound imaging systems to precisely locate said stones or pathological tissue in said living body and controlling the timing and direction of propagation of each timed shockwave pulse via said imaging systems so as to avoid damage to adjacent tissue wherein the directions of propagation between said shockwave pulses has an angle between from about 67° to 105° and wherein said shockwave pulses are generated with a delay time between the two shockwave pulses in the range of 1 millisecond to about 100 milliseconds.

4. A method for fragmenting stones or ablating pathological tissue in a living body or tissue wherein the living body is positioned on a body table having a cutout proximate the location of said stones or pathological tissue in a living body lying on said body table, and two shockwave pulse generators are arranged in cooperative relation to each other and said table such that timed sequential shockwave pulses from said shockwave pulse generators are focused to a focal point at said stones or pathological tissue on or inside the living body or tissue, and one of said shockwave generators contacting said living body through said cutout, using medical x-ray and ultrasound imaging systems to aim and precisely locate said stones or area of treatment in said living body, and controlling the collapse of cavitation bubbles produced by said shockwave pulses by controlling the timing and direction of propagation of each timed shockwave pulse so as to avoid damage to adjacent tissue wherein the directions of propagation between said shockwave pulses has a fixed angle of about 90° and wherein said shockwave pulses are generated with a delay time between the two shockwave pulses in the range of about 1 millisecond to 100 milliseconds.

5. An apparatus for fragmenting stones or ablating pathological issue in a living body comprising:

a body table having a cutout, and two shockwave generators arranged in cooperative relation to each other and said cutout in said body table such that timed sequential shockwave pulses from said shockwave generators are focused to a focal point at said stones or pathological tissue, and one of said shockwave generators being adapted to contact said living body through said cutout, at least two medical imaging systems to precisely locate said stones or pathological tissue for aiming in said living body and means for the timing and direction of propagation of each timed shockwave pulse so as to avoid damage to adjacent tissue wherein the directions of propagation between said shockwave pulses has a fixed angle of about 67° to about 105° and wherein said shockwave pulses are generated with a delay time between the two shockwave pulses in the range of about 1 millisecond to about 100 milliseconds.

6. The apparatus defined in claim 5 wherein said medical imaging apparatus includes x-ray monitoring and ultrasound monitoring systems.

* * * * *